United States Patent
Abrahamson

(10) Patent No.: US 6,368,341 B1
(45) Date of Patent: Apr. 9, 2002

(54) INSERTION ASSEMBLY AND METHOD OF INSERTING A HEMOSTATIC CLOSURE DEVICE INTO AN INCISION

(75) Inventor: Timothy Alan Abrahamson, Seattle, WA (US)

(73) Assignee: St. Jude Medical Puerto Rico, B.V., Amsterdam (NL)

( * ) Notice: Subject to any disclaimer, the term of this patent is extended or adjusted under 35 U.S.C. 154(b) by 0 days.

(21) Appl. No.: 08/906,342

(22) Filed: Aug. 5, 1997

Related U.S. Application Data
(60) Provisional application No. 60/023,368, filed on Aug. 6, 1996.

(51) Int. Cl.[7] ............................................. A61B 17/04
(52) U.S. Cl. ............................ 606/213; 604/15; 604/60
(58) Field of Search ................................. 606/213, 215; 604/60, 285, 288, 15

(56) References Cited

U.S. PATENT DOCUMENTS

| | | | |
|---|---|---|---|
| 3,016,895 A | 1/1962 | Sein | |
| 3,572,335 A | 3/1971 | Robinson | |
| 4,317,445 A | 3/1982 | Robinson | |
| 4,390,018 A | 6/1983 | Zukowski | |

(List continued on next page.)

FOREIGN PATENT DOCUMENTS

| | | |
|---|---|---|
| AU | 651595 | 11/1994 |
| CA | 1322922 | 10/1993 |
| EP | 0139091 | 5/1985 |
| EP | 0401525 | 12/1990 |
| EP | 0476178 | 3/1992 |
| EP | 0482350 | 4/1992 |
| EP | 0493810 | 7/1992 |
| EP | 0527923 | 3/1995 |
| EP | 0474752 | 6/1995 |
| EP | 0422046 | 7/1995 |
| SU | 782814 | 11/1980 |
| WO | 9109641 | 7/1991 |
| WO | 9222252 | 12/1992 |

*Primary Examiner*—Gary Jackson
(74) *Attorney, Agent, or Firm*—Dorsey & Whitney LLP

(57) ABSTRACT

A device and method of closing an incision or puncture in a patient by inserting a hemostatic closure device into the incision or puncture until the distal end of the hemostatic closure device is along the outer wall of the blood vessel or target organ so that the hemostatic closure device does not obstruct the flow of fluid through the blood vessel or target organ. The precise positioning of the hemostatic closure device in the incision or puncture is accomplished through the use of a locating device having a proximal end portion and distally extending locating members thereon which are adapted to be positioned along the outer wall of the blood vessel or target organ of the patient and extend along a relatively small portion of the outer surface of the hemostatic closure device.

25 Claims, 8 Drawing Sheets

U.S. PATENT DOCUMENTS

| | | |
|---|---|---|
| 4,525,157 A | 6/1985 | Vaillancourt .................. 604/52 |
| 4,578,061 A | 3/1986 | Lemelson ................... 604/164 |
| 4,587,969 A | 5/1986 | Gillis |
| 4,588,395 A | 5/1986 | Lemelson ................... 604/59 |
| 4,619,261 A | 10/1986 | Guerriero |
| 4,638,803 A | 1/1987 | Rand |
| 4,645,488 A | 2/1987 | Matukas ...................... 604/59 |
| 4,655,750 A | 4/1987 | Vaillancourt ................ 604/165 |
| 4,744,364 A | 5/1988 | Kensey |
| 4,749,689 A | 6/1988 | Miyata et al. ................. 514/21 |
| 4,772,264 A | 9/1988 | Cragg ........................ 604/158 |
| 4,774,091 A | 9/1988 | Yamahira et al. ............ 424/426 |
| 4,790,819 A | 12/1988 | Li et al. ....................... 604/59 |
| 4,829,994 A | 5/1989 | Kurth |
| 4,832,688 A | 5/1989 | Sagae et al. .................. 605/53 |
| 4,838,280 A | 6/1989 | Haaga ........................ 128/751 |
| 4,852,568 A | 8/1989 | Kensey |
| 4,863,431 A | 9/1989 | Vaillancourt ................ 604/168 |
| 4,871,094 A | 10/1989 | Gall et al. ................... 222/386 |
| 4,878,906 A | 11/1989 | Lindemann et al. ........... 623/1 |
| 4,895,564 A | 1/1990 | Farrell ....................... 604/164 |
| 4,900,303 A | 2/1990 | Lemelson ................... 604/54 |
| 4,904,240 A | 2/1990 | Hoover ....................... 604/53 |
| 4,929,246 A | 5/1990 | Sinofsky ......................... 606/8 |
| 4,936,835 A | 6/1990 | Haaga ........................ 604/265 |
| 4,941,874 A | 7/1990 | Sandow et al. ............... 604/60 |
| 4,950,234 A | 8/1990 | Fujioka et al. ................ 604/60 |
| 4,961,729 A | 10/1990 | Vaillancourt ................ 604/164 |
| 4,994,028 A | 2/1991 | Leonard et al. ............... 604/60 |
| 5,021,059 A | 6/1991 | Kensey et al. .............. 606/213 |
| 5,053,046 A | 10/1991 | Janese ........................ 606/215 |
| 5,061,274 A | 10/1991 | Kensey ....................... 606/213 |
| 5,080,655 A | 1/1992 | Haaga ........................ 604/265 |
| 5,108,421 A | 4/1992 | Fowler ....................... 606/213 |
| 5,129,882 A | 7/1992 | Weldon et al. ................ 604/96 |
| 5,192,302 A | 3/1993 | Kensey et al. .............. 606/213 |
| 5,195,988 A | 3/1993 | Haaga ........................ 604/265 |
| 5,222,974 A | 6/1993 | Kensey et al. .............. 606/213 |
| 5,254,105 A | 10/1993 | Haaga ........................ 604/265 |
| 5,282,827 A | 2/1994 | Kensey et al. .............. 606/215 |
| 5,306,254 A | 4/1994 | Nash et al. .................. 604/168 |
| 5,312,435 A | 5/1994 | Nash et al. .................. 606/213 |
| RE34,866 E | 2/1995 | Kensey et al. .............. 606/213 |
| 5,392,918 A | 2/1995 | Harrison ..................... 206/571 |
| 5,411,520 A | 5/1995 | Nash et al. .................. 606/213 |
| 5,441,517 A | 8/1995 | Kensey et al. .............. 606/213 |

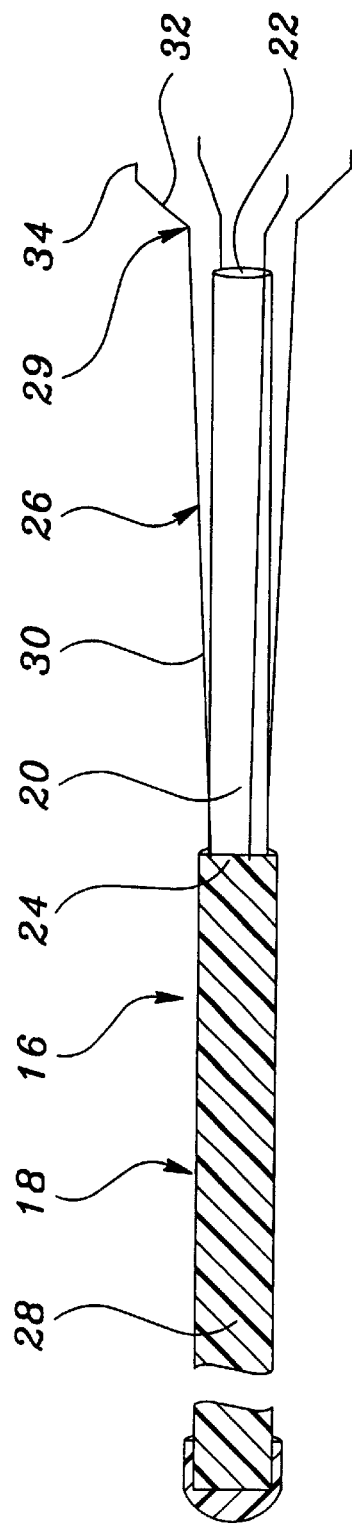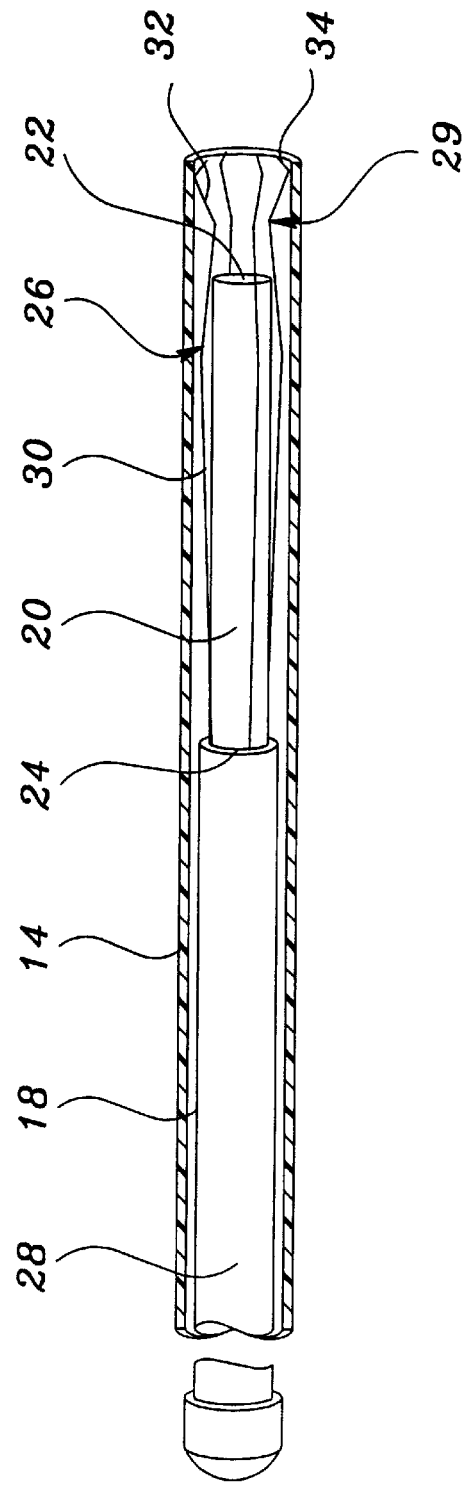

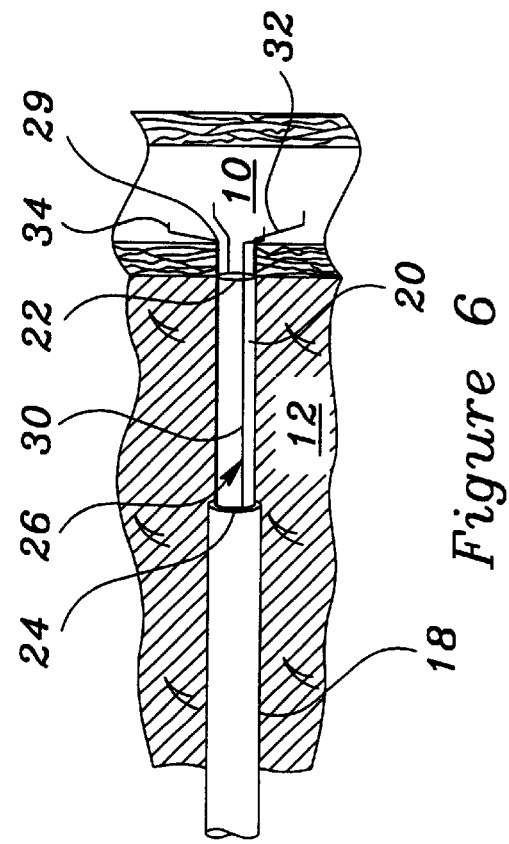
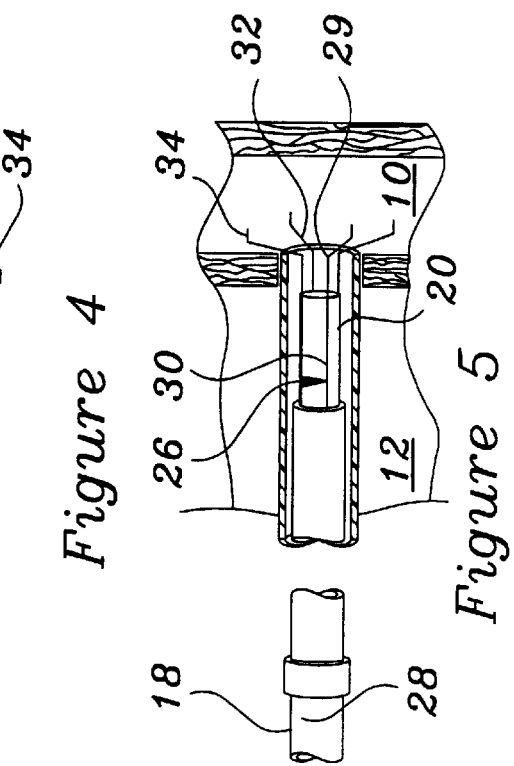
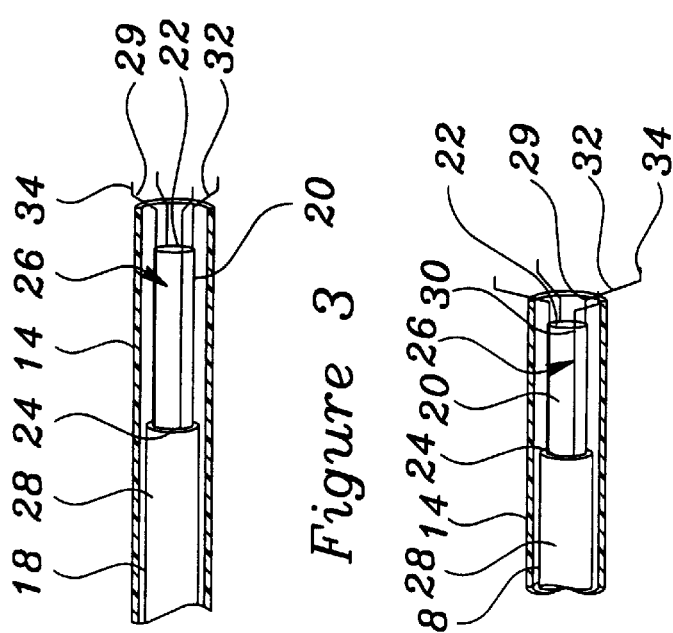

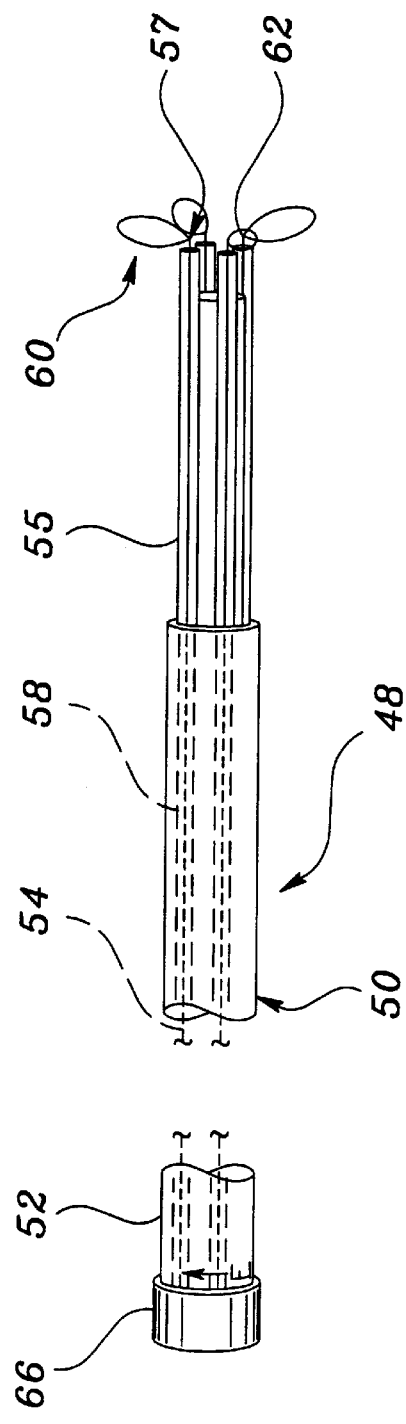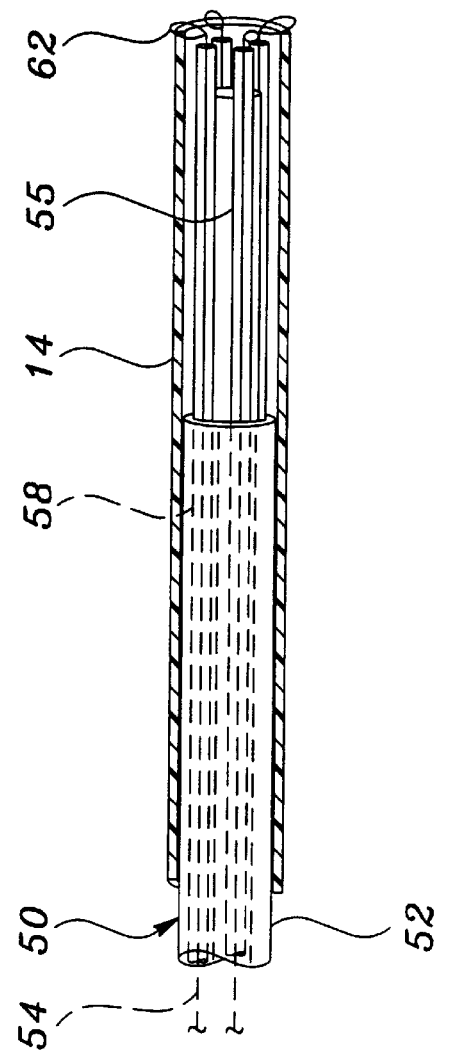

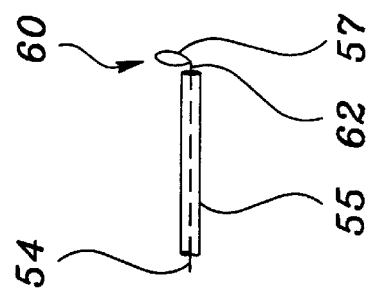
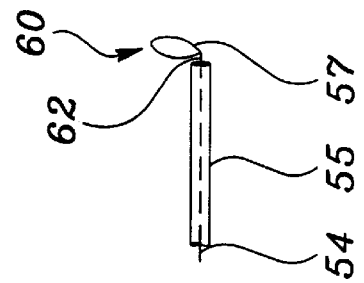
Figure 12
Figure 13
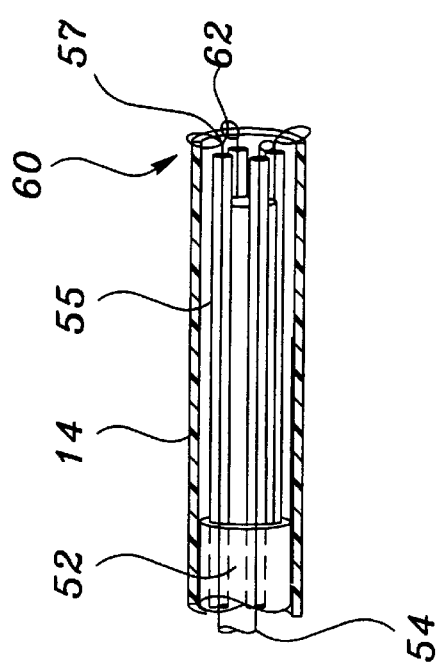
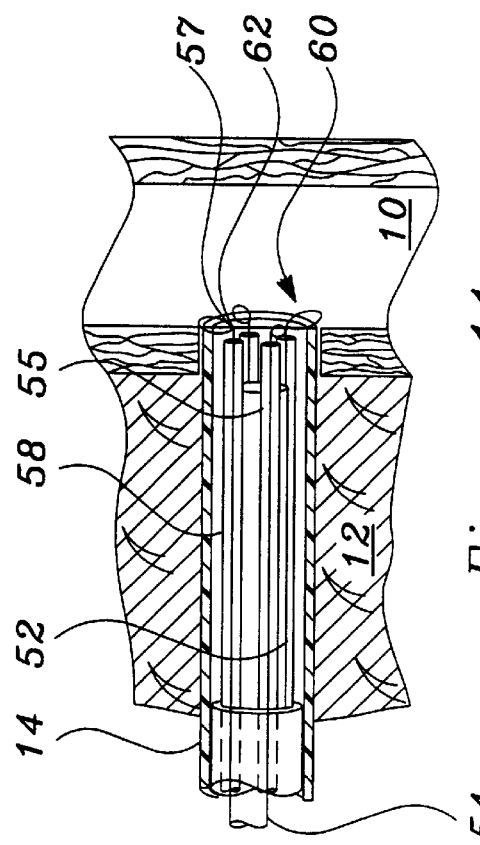
Figure 10
Figure 11

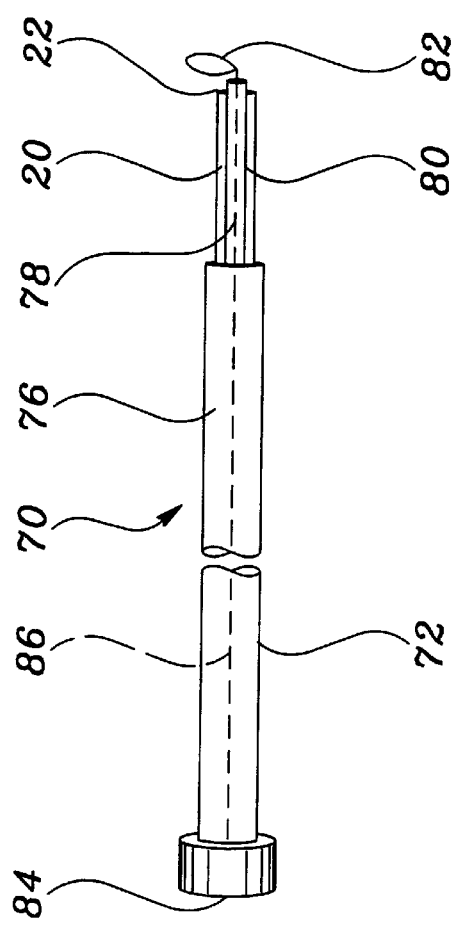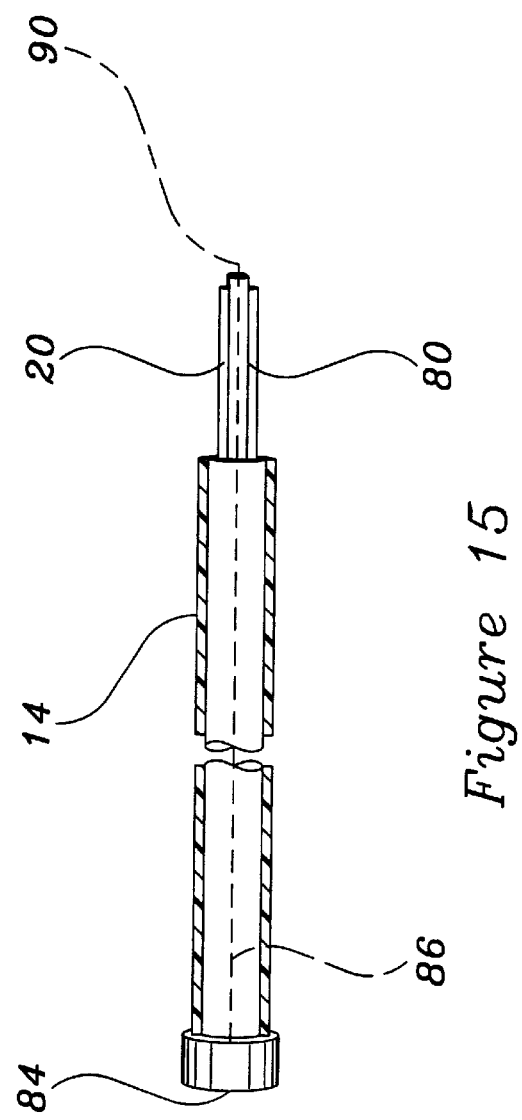

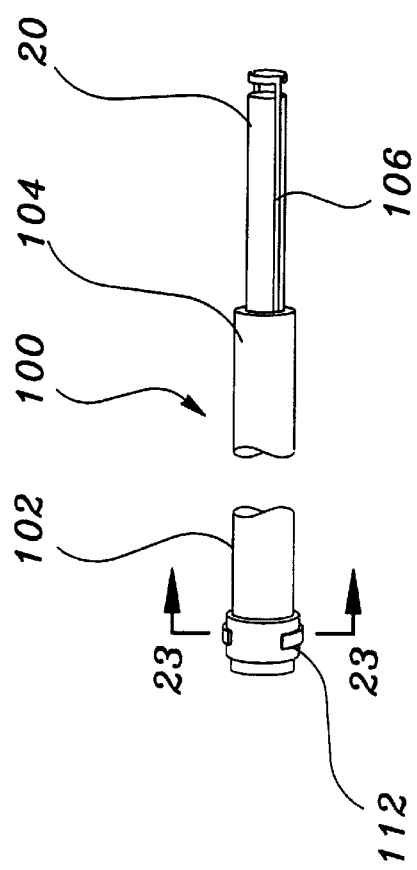
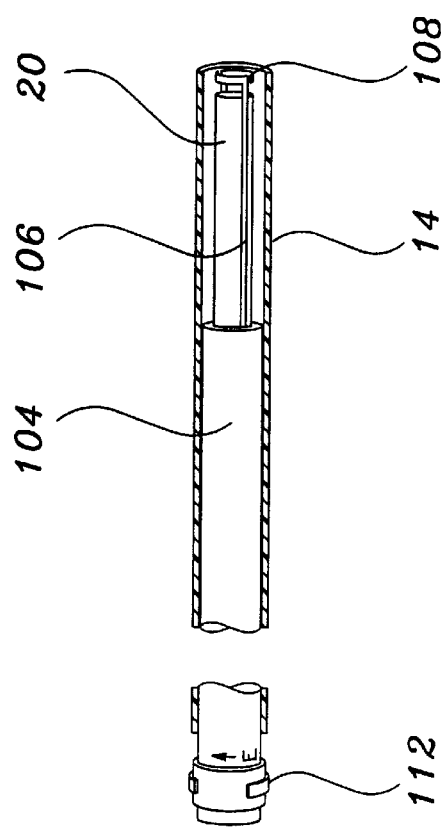
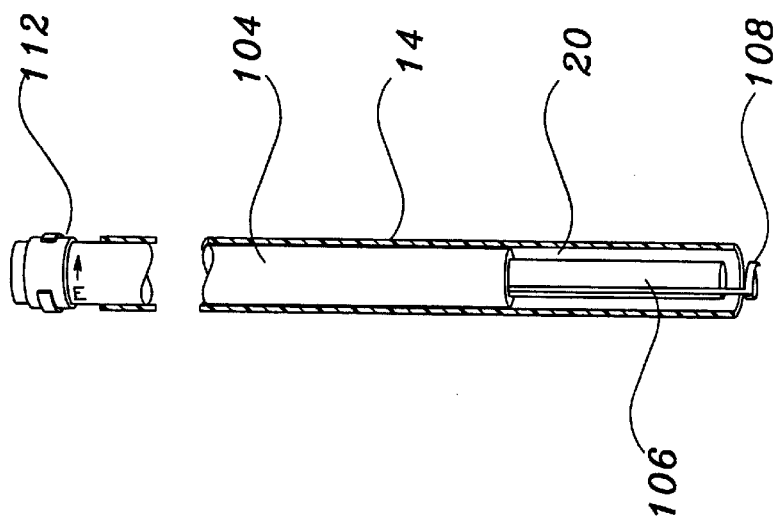

INSERTION ASSEMBLY AND METHOD OF INSERTING A HEMOSTATIC CLOSURE DEVICE INTO AN INCISION

This application is a provision of Ser. No. 60/023,368 filed Aug. 6, 1996.

FIELD OF THE INVENTION

The present invention relates generally to hemostatic devices and more particularly to an insertion assembly and hemostatic closure device which are insertable into an incision or puncture formed in the body of a patient to seal the incision from the flow of body fluids therethrough.

BACKGROUND OF THE INVENTION

During catheterization or other medical procedures, a physician will create an opening into an artery or other blood vessel of a patient with a conventional catheter introducer or dilator. The size of the opening will vary depending on the type of procedure and the size of the catheter which is to be used. For example, the diameter of the catheter and catheter sheath used in standard angiography procedures is typically between 5 to 8 French (1.67 mm and 2.67 mm, respectively). The diameter of the catheter and catheter sheath used in angioplasty procedures and an increasing number of stent placement procedures may be about 8 (2.67 mm) or 9 (3.33 mm) French. The diameter of the catheter and catheter sheath used in intro-aortic balloon pump procedures is typically between 14 to 16 French (4.67 mm and 5.33 mm, respectively) and the diameter of the catheter and catheter sheath used with cardiopulmonary support systems is typically between 18 and 20 French (6.0 mm and 6.67 mm, respectively). Additionally, the catheter may often be twisted or otherwise manipulated as it is advanced to the treatment site, thereby causing a further enlargement of the incision or puncture in the body of the patient.

When the medical procedure is completed and the catheter is removed from the artery or other blood vessel, the conventional practice has been to apply external pressure to the entry site until clotting occurs. Because many of the patients undergoing these procedures have been medicated with an anticoagulant such as heparin, the nurse may be required to apply external pressure to the incision site for an extended period of time. The time required to stop bleeding at the incision is not an efficient use of the nurses time and a painful hematoma or unsightly bruise may still occur at the incision site because the artery will continue to bleed internally until clotting blocks the opening in the artery.

U.S. Pat. No. 4,829,994 granted to Kurth on May 16, 1989, attempts to resolve the above-described problem by providing an apron-like device consisting of a pelvic apron and a groin strap to apply a compressive force to the femoral vessel of the patient. Although this device effectively eliminates the need to have a nurse apply direct pressure to the incision site, a decrease in blood flow through the femoral artery may be caused by the use of this device and may increase the likelihood of clot formation in the compromised patient.

Another approach to resolving the above-identified problem is disclosed in U.S. Pat. No. 4,929,246 granted to Sinofsky on May 29, 1990. The method of using the device disclosed in this patent includes the steps of advancing a semi-rigid tube having an inflatable balloon at its distal end through the overlying tissue to a location adjacent to the outer wall of the punctured artery. The balloon is then inflated to apply pressure directly to the outer wall of the artery. Laser energy is then directed to the outer wall of the artery via an optical fiber centrally located in the semi-rigid tube such that the laser energy passes through the optical fiber and balloon of the semi-rigid tube to thermally weld the artery and seal the incision.

A further approach to resolving the above-identified problems is disclosed in U.S. Pat. No. 4,744,364 granted to Kensey on May 17, 1988, and related U.S. Pat. Nos. 4,852,568 and 4,890,612 granted to Kensey on Aug. 1, 1989, and Jan. 2, 1990, respectively. The first two Kensey patents disclose a device for sealing an opening in the wall of a blood vessel which consists of an elongate tubular body having an expandable closure member removably disposed therein. The tubular body also includes an ejecting device disposed within the tubular body for forcing the closure member from the tubular body into the interior of the blood vessel. A retraction filament is secured to the closure member so that the engagement surface of the closure member hemostatically engages the inner surface of the blood vessel contiguous with the puncture. The '612 Kensey patent discloses a device which includes an elongate absorbable member having a holding portion which is adapted to engage portions of the tissue adjacent to the punctured vessel or organ to hold the plug member in place and a sealing portion formed of a foam material which extends into the punctured vessel or organ to engage the tissue contiguous therewith to seal the puncture. Subsequent patents granted to Kensey et al. are illustrative of improvements to the basic approach described above and generally include an anchor member which is used in combination with a suture and a collagen member to seal an incision or blood vessel.

U.S. Pat. No. 5,108,421 granted to Fowler and assigned to the assignee of the present invention, discloses the use of a "vessel plug" type approach wherein the hemostatic closure device is inserted into the incision of the patient and may be positioned in the incision using a locating member such as an elongate balloon type member or a syringe type device. U.S. Pat. No. 5,391,183 granted to Janzen et al. discloses another vessel plug type approach wherein one or more hemostatic closure devices are inserted into the incision using a device with a plunger member. None of the prior art devices teach the use of a simple and relatively inexpensive means for reliably effecting the closure of a puncture or incision in the wall of a blood vessel, duct or organ to significantly reduce the time to ambulation of a patient as well as to reduce the risk of hematoma or clot formation.

SUMMARY OF THE INVENTION

Accordingly, it is an object of the present invention to provide a device and method of use which overcomes the disadvantages of the prior art.

It is another object of the present invention to reduce the time required for sealing an incision in an artery and to decrease the likelihood that a hematoma will form after the catheter is removed from the incision.

It is yet another object of the present invention to provide simple, reliable and easy to use device for locating the wall of a blood vessel, duct or organ using the locating device of the present invention.

These and other objects of the present invention are achieved by providing a device and method for sealing an incision in a blood vessel, duct or organ using the device as described hereinafter.

One form of the present invention preferably includes a sealing assembly consisting of a relatively small diameter locating device which is used in conjunction with a conventional access sheath. The locating device preferably includes one or more wire locating members thereon and a porous, absorbable hemostatic closure device. The hemostatic closure device includes a distal end which is preferably sized and shaped so that the distal end of the hemostatic closure device may be positioned generally along and proximally of the outer surface of the blood vessel duct or lumen so that the hemostatic closure device will not enter into the blood vessel and potentially cause a disruption in the flow of fluid past the incision. The method of using the preferred form of the present invention includes the steps of inserting the sealing assembly into the incision through an access sheath which has been previously used to perform the medical procedure and which is positioned to extend a short distance into the blood vessel of the patient. The sealing assembly is advanced in the access sheath until the locating members extend slightly beyond the distal end of the access sheath and in the blood vessel. The locating members on the distal end of the locating device are then positioned to extend laterally from the distal end of the locating device. The entire assembly including the sealing assembly and the access sheath is then withdrawn slightly in the incision and blood vessel until the locating members contact the distal side of the blood vessel wall. The access sheath is then removed from the incision to expose the hemostatic closure device to the blood and other fluids in the incision. This exposure of the hemostatic closure device to blood or other fluids allows the hemostatic closure device to absorb fluids in the incision and from the surrounding tissue while allowing the hemostatic closure device to expand in the incision. Finally, the locating members may be withdrawn from the incision without disturbing the position of the hemostatic closure device in the incision. A dressing may then be placed over the incision site to protect the incision while the hemostatic closure device is incorporated into the surrounding tissue.

An advantage of the present invention is that the hemostatic closure device does not extend into the blood vessel, duct or organ and therefore, the flow of fluid through the vessel is not obstructed by the hemostatic closure device.

Another advantage of the present invention is that locating device of the present invention may be used to reliably position the distal end of the hemostatic closure device generally along or proximally of the proximal surface of the wall of the blood vessel without significantly obstructing the blood vessel, duct or organ of the patient.

Yet another advantage of the present invention is that the locating members of the locating device of the present invention preferably extend around less than one half of the circumference of the hemostatic closure device and more preferably less than one fourth of the circumference of the hemostatic closure device.

BRIEF DESCRIPTION OF THE DRAWINGS

FIG. 1 is a side elevational view, partially in cross section, showing the sealing assembly of the present invention;

FIG. 2 is a side elevational view, partially in cross section, showing the sealing assembly of the present invention positioned in an access sheath;

FIG. 3 is a side elevational view, partially in cross section, showing the locating members of the locating device partially extending from the access sheath;

FIG. 4 is a side elevational view, partially in cross section, showing the locating members of the locating device fully extended from the access sheath;

FIG. 5 is a side elevational view, partially in cross section showing the sealing assembly of the present invention with the locating members fully extended and positioned along the inner wall of the patient's blood vessel;

FIG. 6 is a side elevational view, partially in cross section showing the hemostatic closure device of the sealing assembly of FIG. 1 after the access sheath has been removed from the patient and having the sealing assembly in position in the incision;

FIG. 7 is a side elevational view, partially in cross section showing the hemostatic closure device of the sealing assembly of FIG. 1 in the incision after the access sheath and locating device have been removed from the patient;

FIG. 8 is a side elevational view, partially in cross section, showing an alternate form of the sealing assembly of the present invention;

FIG. 9 is a side elevational view, partially in cross section, showing the locating members of the alternate form of the locating device partially extending from the access sheath;

FIG. 10 is a side elevational view, partially in cross section, showing the locating members of the alternate form of the locating device fully extended from the access sheath;

FIG. 11 is a side elevational view, partially in cross section showing the sealing assembly of FIG. 8 with the locating members of the alternate form of the locating device fully extended and positioned along the inner wall of the patient's blood vessel;

FIG. 12 is a partial enlarged side elevational view showing one of the locating members and guideways of the alternate form of the locating device in the retracted position;

FIG. 13 is a partial enlarged side elevational view showing one of the locating members and guideways of the alternate form of the locating device in the extended position;

FIG. 14 is a side elevational view, partially in cross section, showing a further alternate form of the sealing assembly of the present invention;

FIG. 15 is a side elevational view, partially in cross section, showing the locating members and guideways of the alternate form of the locating device of FIG. 14 with the sealing assembly positioned in the access sheath;

FIG. 20 is a side elevational view, partially in cross section, showing a further alternate form of the sealing assembly of the present invention;

FIG. 21 is a side elevational view, partially in cross section, showing the locating members of the alternate form of the locating device of FIG. 20 with the sealing assembly positioned in the access sheath;

FIG. 22 is a side elevational view, partially in cross section, showing the guideways and locating members with locating members of the locating device of FIG. 20 fully extended from the access sheath;

DETAILED DESCRIPTION OF THE PRESENT INVENTION

Figure 18:
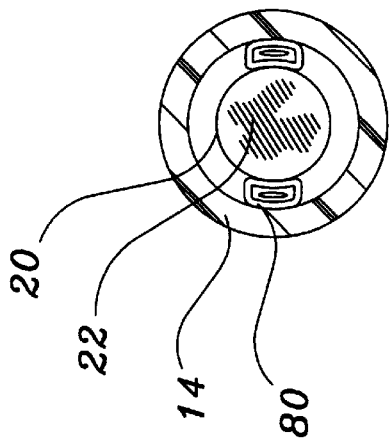
FIG. 18 is a bottom view of the distal end of the sealing assembly of FIG. 14 with the locating members shown in the retracted position.
Figure 19:
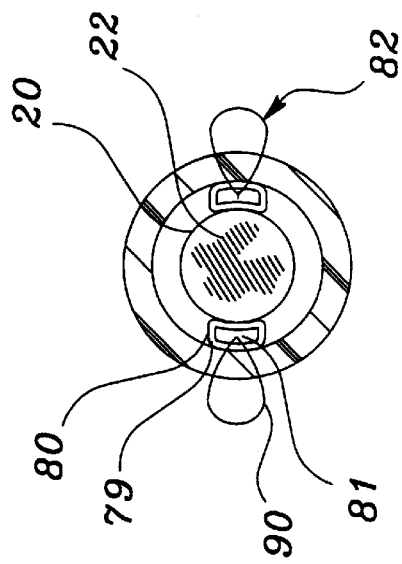
FIG. 19 is a bottom view of the distal end of the sealing assembly of FIG. 14 with the locating members shown in the extended position.

The present invention is described hereinafter with specific reference to the use of the present invention for sealing an incision or puncture in a blood vessel such as the femoral artery 10 of a patient. It is contemplated that the sealing assembly 16 of the present invention may be used with nearly any catheterization or other medical procedure wherein it is desirable to seal an incision or puncture to prevent the loss of the patient's body fluid therethrough, including laparoscopic or similar procedures. Additionally, the locating device 18 of the present invention may be used with nearly any catheterization or other medical procedure wherein it is desirable to reliably locate the lumen of a blood vessel, duct or target organ of a patient's body to prevent the loss of the patient's body fluid therethrough, including laparoscopic, endoscopic, intracardiac or similar procedures. As used herein, the distal end of an element is referred to as the end of the element nearest to the patient and the proximal end of an element is referred to as the element furthest from the patient.

In order to more fully understand and appreciate the present invention, a brief description of a conventional angiographic catheterization procedure through the femoral artery of the patient is set forth herein. In such a procedure, an angiographic needle (not shown) is inserted percutaneously through the epidermal and dermal layer of the skin 12 of the patient at a preferred angle of approximately 25 to 45 degrees. The needle is inserted between about 6 mm and 70 mm percutaneously into the skin of the patient until the needle pierces the femoral artery. The puncture of the artery 10 by the needle is then confirmed by the physician and a small diameter guide wire (not shown) is inserted through the needle for a distance of approximately 15 to 20 cm. The needle is then withdrawn over the guidewire while pressure is applied to the artery 10 to limit the bleeding and prevent the formation of a hematoma at the incision site. A dilator (not shown) and an outer introducer or catheter access sheath 14 are inserted over the guidewire and the guidewire is then removed from the inside of the dilator. Next, the catheter is advanced through the access sheath 14 to the final desired location and the procedure is performed. Once the procedure has been completed, the catheter is removed and only the access sheath 14 remains in the incision to allow the sealing assembly 16 which includes the locating device 18 and hemostatic closure device 20 of the present invention to be inserted into the incision as described hereinafter.

As shown in FIGS. 1–7, a preferred form of the present invention consists generally of the preloaded sealing assembly 16 which includes the locator device 18 and the hemostatic closure device 20. As shown in FIGS. 3–5, the hemostatic closure device 20 of the present invention is preferably a cylindrical rod-shaped member which is constructed of a porous, biodegradable and expandable hemostatic collagen sponge although a synthetic collagen type complex or a polymerized polylactic acid, or polyglycolic acid matrix or similar bioabsorbable materials may also be used. The distal end 22 of the hemostatic closure device 20 may be preferably oriented at an angle of approximately 25 to 45 degrees with respect to the lengthwise dimension of the hemostatic closure device 20 to conform to the typical angle of access used in the medical procedure. The distal end 22 may also be allowed to soften by absorbing fluids from the incision to comply with the shape of the vessel wall without a particular orientation with respect to the incision. The proximal end 24 of the hemostatic closure device 20 may be excised after placement in the patient and positioned at or slightly below the epidermal layer of the patient's skin. The hemostatic closure device 20 may also be sized to extend proximally of the blood vessel wall or a further hemostatic closure device may be inserted into the incision as desired or as desired to obstruct the flow of fluids through the incision.

The locating device 18 of the present embodiment consists of a proximally positioned and generally cylindrically shaped delivery member 28 which, in the present embodiment, includes the proximal ends of the locating members 26 fixedly retained therein. As shown, the locating members 26 are preferably formed of a small diameter wire or similar material having flexibility and structural memory. The locating members 26 extend distally from the delivery member 28 and include one or more predetermined bends or curved areas 29. In this embodiment, the locating device 18 preferably includes four locating members 26 thereon although one or more locating members 26 are believed to be sufficient to provide the resistance necessary to perform the locating function as described below. For example, a single locating wire 26 or member may be sufficient to provide the desired resistance, if the locating device 18 is rotated to be oriented at an acute or perpendicular angle with respect to the blood vessel.

As shown in FIG. 1, each of the locating members 26 of the present embodiment include an elongate proximal portion 30 which is oriented longitudinally along the lengthwise dimension of the locating device 18 and are positioned to extend along the outer dimension of the hemostatic closure device 20 in use. The distal end portion of the locating member 26 includes a distal leg member 32 which is prestressed by a bend area 29 in the locating member 26 to extend generally perpendicular to the proximal portion 30 in the unstressed state as shown in FIG. 1. The leg members 32 each include a foot member 34 thereon which may take the form of a generally perpendicular reverse bend as shown in FIG. 1 or may be small loop or similar members which are shaped and formed to minimize any potential damage to the blood vessel and/or incision. As shown in FIG. 2, when the locating device 18 is positioned in the access sheath 14, the proximal portion 30 of the locating members 26 are positioned adjacent to and generally along the outer dimension of the hemostatic closure device 20. The leg members 32 of the locating members 26 are stressed by the access sheath 14 and extend longitudinally beyond the distal end 22 of the hemostatic closure device 20 along the lengthwise dimension thereof. In this position, the leg members 32 function to fixedly retain the hemostatic closure device 20 in the desired position in the locating device 18 to ensure proper placement of the hemostatic closure device 20 in the incision as described below. The bend area 29 of the locating member 26 is stressed when the locating member is in the access sheath 14 and causes the leg member 32 to contact the distal end portion 22 of the hemostatic closure device 20. The bend area 29 of the locating members 26 will lightly press along the access sheath 14 so that the leg members 32 retain the distal portion of the hemostatic closure device 20 in the desired position relative to the locating members 26 to ensure the proper positioning of the hemostatic closure device in the incision as described below. This holding feature of the present embodiment of the locating members 26 is caused by the tendency of the bend areas 29 to move from the stressed position shown in FIG. 2 to their natural unstressed position as shown in FIG. 1.

As described briefly above, the hemostatic closure device 20 of the preferred embodiment initially swells when it is placed in the incision to absorb fluid in the incision and surrounding tissue and also prevents the formation of a hematoma at the incision site. Additionally, the porosity of the desired hemostatic closure device 20 may vary depending on the anticipated size of the incision so that the fluids from the surrounding tissue may be absorbed more rapidly if a larger incision is made or if it is necessary for the hemostatic closure device 20 to expand more quickly such as in the situation when the patient is highly anticoagulated. Similarly, the porosity of the hemostatic closure device 20 may be varied along the lengthwise or cross sectional dimension of the hemostatic closure device 20 depending on the anticipated use of the hemostatic closure device 20 so that portions of the hemostatic closure device 20 may swell or be absorbed more quickly than other portions of the hemostatic closure device 20 in the incision. Furthermore, the porosity and consistency of certain portions of the hemostatic closure device 20 may be varied to provide the desired capability for connective tissue cell infiltration into the hemostatic closure device 20 so that the patient's tissue will ultimately fill the percutaneous incision at various rates according to the selected porosity of the hemostatic closure device 20. The porosity of the hemostatic closure device may also be selected to allow the hemostatic closure device to be inserted into and conform to the incision to promptly obstruct the incision and seal the incision from the flow of fluids through the incision without affecting the flow of fluids through the blood vessel. By positioning the distal end 22 of the hemostatic closure device 20 at or near the outer wall surface or lumen of the artery 10, there is no disruption of the fluid flow through the artery 10 at the incision site and the risk of thrombosis is minimized as compared to prior devices which include a closure or sealing member which may be positioned along the inner wall of the artery 10. It is anticipated that the hemostatic closure device 20 will degrade and be absorbed into the surrounding tissue within a few weeks or months so that there is no need to remove the hemostatic closure device 20 from the incision at a later date.

Additionally, the hemostatic closure device 20 may be formulated to include a conventional clotting agent, such as a tissue thromboplastin, which is incorporated in at least a portion of the collagenous material to accelerate local hemostasis and which will allow the physician to maintain the patient on an anticlotting agent such as heparin after the procedure has been performed. It is further anticipated that the hemostatic closure device 20 may be formulated to include a radiopaque material therein to allow the placement of the hemostatic closure device 20 to be observed using conventionally visualization methods.

Once the angiographic or other medical procedure has been performed and the catheter is removed from the patient, the introducer or access sheath 14 remains in the incision as shown in FIG. 2. The access sheath 14 functions to maintain the incision open while the sealing assembly 16 is inserted therethrough. Once the user verifies that the access sheath 14 is properly positioned in the incision with the distal end of the access sheath 14 extending a short distance into the artery 10, the user may insert the sealing assembly 16 into the access sheath 14 and blood vessel by pushing the sealing assembly 16 distally with respect to the access sheath 14 until the locating members 26 of the locating device 18 extend laterally a short distance from the distal end of the access sheath 14.

With this insertion approach, when the locating members 26 approach the partially extended position shown in FIG. 3, the tendency of the locating members 26 to reach the unstressed and extended position causes a slight springing effect which indicates to the user that the locating members 26 of the locating device 18 have reached the extended position as shown in FIG. 4. Alternately, markings or other visually observable, tactile or audible indicators (not shown) may be part of the access sheath or the locating device to indicate to the user when the locating members 26 are in the retracted and/or extended positions.

Once the locating members 26 are in the extended position, the access sheath 14 and sealing assembly 16 are withdrawn proximally in the incision until the extended locating members 26 contact the wall of the blood vessel as shown in FIG. 5. The locating members 26 are designed to provide a sufficient amount of resistance to continued proximal movement of the locating device 18 so that the user is provided with a readily detectable indication that the locating members 26 are in contact with the wall of the blood vessel while also having sufficient flexibility to allow the user to reposition the locating device 18 in the incision if necessary. Additionally, the locating members are designed to minimize damage to the blood vessel wall and incision during use.

Once the location of the wall of the blood vessel is identified, the access sheath 14 may be removed or withdrawn partially from the incision to expose the hemostatic closure device 20 to the fluids present in the incision. As the hemostatic closure device 20 of the present invention absorbs fluids in the incision, the hemostatic closure device 20 expands to fill the incision and obstruct the flow of fluids therethrough. After a short period of time, the user may fully withdraw the locating device 18 and access sheath 14 from the incision without disturbing the precise positioning of the hemostatic closure device 20 in the incision. As shown best in FIGS. 1 and 5, the hemostatic closure device 20 is positioned in a predetermined position in the locating device 18 prior to use. This preferred position of the hemostatic closure device 20 in the locating device 18 is proximal to the leg members 32 of each of the locating members 26 to ensure that the hemostatic closure device 20 is precisely positioned in the incision without extending into the blood vessel of the patient when the leg members 32 are in the extended position along the wall of the blood vessel.

As with the preferred embodiment shown in FIGS. 1–7, an alternate embodiment of the present invention is shown in FIGS. 8–13. In this embodiment, the previously inserted access sheath 14 is retained in the incision after the procedure has been performed. The preloaded sealing assembly 48 is then inserted into the incision through the access sheath 14 in a manner similar to the embodiment described above.

The sealing assembly 48 of the present embodiment generally consists of the locating device 50 and the hemostatic closure device 20. The locating device 50 generally includes a proximally positioned and generally cylindrically shaped delivery member 52 which, in the present embodiment, includes the proximal ends of the locating members 54 slidably retained therein. As shown, the locating members 54 extend distally from the delivery member 52 through elongate and cylindrically shaped guide members 55. The distal ends of the locating members 54 include one or more predetermined bends or curved areas 57. In this embodiment, the locating device 50 preferably includes four elongate, small diameter locating members 54 thereon although one or more locating members 54 are believed to be sufficient to perform the locating function as described below. As shown in FIGS. 12 and 13, each of the locating members 54 include an elongate straight proximal portion 56 which is oriented to extend longitudinally along and through the passageways 58 formed lengthwise along the delivery member 52 of the locating device 50. The locating members 54 extend distally from the distal end of the delivery member 52, through the guide members 55 and are aligned to extend generally lengthwise and along the outer dimension of the hemostatic closure device 20 in use. The distal end portion of each locating member 54 includes a distal leg member which is formed to assume a generally loop shaped configuration 60 in the extended position of the present embodiment. The loop members 60 of the present embodiment preferably consist of a small diameter wire member having an end portion 62 which is fixedly connected along the distal end of the respective guideway 55. The loop members 60 may be formed with a crimp or small bend 57 along the locating members 54 such that when the locating member 54 is moved from the retracted position (FIG. 12) to the extended position (FIG. 13), the loop member 54 bends to extend laterally from the distal end of the guideway 55 and access sheath 14 and is oriented to extend generally perpendicular to the longitudinal axis of the sealing assembly 48. As with the prior embodiment, it may be useful to rotate the locating device 50 prior to locating the blood vessel wall to enable at least one of the loop members 54 to form an acute angle with the wall of the blood vessel to create an increased resistance when the loop member 54 contacts the wall of the blood vessel.

As shown in FIG. 8, when the locating device 50 is positioned in the access sheath 14, the proximal portion 56 of the locating members 54 are positioned proximally of and along the outer lengthwise dimension of the hemostatic closure device 20 in the guide members 55. The distal end of the locating device 50 is located generally adjacent to or slightly distally of the distal end of the access sheath 14. When the locating members 54 are moved to the extended position, the bend areas 57 in the locating members 54 cause the loop members 60 to extend laterally and longitudinally beyond the distal end 22 of the access sheath 14, guide members 55 and the hemostatic closure device 20. Because the portion of the locating member 54 along the bend area 57 does not extend beyond the distal end of the delivery member 52 until the loop members 60 are in the extended position, the bend area 57 of each of the locating members 54 causes the guide members 55 to bend slightly and contact the distal end portion 22 of the hemostatic closure device 20 prior to the loop members 60 reaching the extended position. Therefore, the combination of the guide members 55 and the bend area 57 of the locating members 54 function to retain the hemostatic closure device 20 in the desired position prior to final placement in the incision.

As shown best in FIG. 8, the proximal portion of the delivery member 52 includes a circular band member 66 therearound. The circular band member 66 is connected to the proximal end of the proximal portion 56 of the locating members 54 to allow for the extension and retraction of the locating members 54 upon the distal or proximal movement of the band member 66 along the delivery member 52. Although, the movement of the locating members 54 is described as being through the distal or proximal movement of the band member 66 along the proximal portion of the delivery member 52, it is anticipated that this type of movement may also be accomplished by a rotary knob, sliding levers or other convenient methods of imparting the desired movement to the locating members 54. Additionally, although the passageways 58 and guide members 55 of the present embodiment are shown as containing the locating members 54 extending therethrough, it is anticipated that the passageways and/or guide members may include a lubricous coating or lining therein and/or the locating members 54 may include a coating thereon to minimize the frictional resistance to the movement of the locating members between the retracted and extended positions.

Once the angiographic or other medical procedure has been performed and the catheter is removed from the patient, the introducer or access sheath 14 retained in the incision as shown in FIG. 8 to maintain the incision open while the sealing assembly 48 of the present embodiment is inserted therethrough. Once the user confirms that the access sheath 14 is properly positioned in the incision with the distal end of the access sheath 14 extending a short distance into the artery 10, the user may insert the sealing assembly 48 into the incision and blood vessel by pushing the sealing assembly 48 distally while holding the access sheath 14 steady until the distal end of the locating members 54 of the locating device 50 extend slightly beyond the distal end of the access sheath 14. In the present embodiment, the length of the locating device 50 and the access sheath 14 are tightly controlled to allow the user to readily determine when the locating members 54 are properly positioned with respect to the distal end of the access sheath 14 as shown in FIG. 9. For example, the outer surface of the locating device 50 may include markings thereon (not shown) or other visually or physically observable indications of when the locating device 50 is properly aligned with respect to the access sheath 14. When the distal end of the guide members 55 and the locating members 54 are positioned along the distal end of the access sheath 14 in the retracted position, the loop members 60 may be formed by moving the band member 66 distally along the locating device 50 to extend the loop members 60 until the bend areas 57 are exposed such that the loop members 57 extend generally perpendicularly from the distal end of the access sheath 14 and into the blood vessel of the patient. As described above, the locating device 50 preferably includes an indication along the band member 66 to indicate to the user that the bend 57 of the locating members 54 have cleared the distal end of the guide members 55 and the loop members 60 are fully extended in the blood vessel of the patient. This may be formed to provide the user with visual, tactile and or audible indications that the loop members 60 have been fully and successfully extended.

Once the locating members 54 are moved to the extended position by sliding the band member 66 distally along the delivery member 52, the locating device 50 and access sheath 14 may be moved proximally in the incision until the extended loop members 60 contact the wall of the blood vessel as shown in FIG. 11. As with the prior embodiment, the locating members 54 are designed to provide the user with a sufficient indication of the contact between the loop members 60 and the wall of the blood vessel while minimizing damage to the wall of the blood vessel or incision if the locating device 50 is inadvertently or prematurely removed from the incision without retracting the locating members 54. Once the loop members 60 are positioned along the wall of the blood vessel, the access sheath 14 may be withdrawn partially or fully from the incision to allow the hemostatic closure device to absorb fluids in the incision and surrounding tissue. The band member 57 may then be moved proximally along the delivery member 52 until the locating members 54 are in the retracted position. Thereafter, the locating device 50 may be removed from the incision while the hemostatic closure device 20 remains in the incision to obstruct the flow of fluids therethrough. Alternately, the band member 57 may remain in the distal position or may be moved proximally along the delivery member 52 until the locating members 54 are in a partially retracted position and then the access sheath and delivery member 52 may be removed from the incision together.

As with the prior embodiment, the hemostatic closure device 20 is designed to absorb fluids in the incision. The absorption of fluids by the hemostatic closure device 20 causes the hemostatic closure device 20 to resist movement in the incision as the locating members 54 are removed from the incision. In this embodiment, the external surface of the guide members 55 contact only a relatively small amount of the external surface of the hemostatic closure device 20 so that the portion of the hemostatic closure device 20 between the guide members 55 are allowed to absorb fluids in the incision and from the surrounding tissue to provide frictional resistance to movement as the locating device 50 is removed from the incision. Additionally, the external surface of the guide members 55 may be coated with a lubricous coating, such as various commercially available hydrophilic and/or water activated coatings, to increase to lubricity of the external surface of the guide members 55 to ease the removal of the locating device 50 from the incision, while not affecting the final positioning of the hemostatic closure device 20 in the incision.

As with the prior embodiment, the distal end 22 of the hemostatic closure device 20 is positioned in the incision at or along the outer wall of the blood vessel or artery 10 so that none of the hemostatic closure device 20 extends into the blood vessel 10 to disrupt the flow of blood therethrough. The porosity of the hemostatic closure device 20 is preferably chosen so that the hemostatic closure device 20 will rapidly expand as it absorbs fluids from the surrounding tissue and so that the hemostatic closure device 20 will degrade in a matter of weeks or months. Because the hemostatic closure device 20 does not extend into the lumen of the blood vessel 10, the hemostatic closure device 20 of the present embodiment may include a clotting agent incorporated therein to promote localized hemostasis in the incision without increasing the likelihood of thrombosis formation in the blood vessel 10.

FIGS. 14–19 are illustrative of a further embodiment sealing device 70 of the present invention. As with the prior embodiments described above, this embodiment is used after the medical procedure has been performed. In this embodiment, the previously inserted access sheath 14 is retained in the incision after the procedure has been performed. The preloaded sealing assembly 70 is then inserted into the incision through the access sheath 14 in a manner similar to the embodiments described above.

The sealing assembly 70 of the present embodiment generally consists of the locating device 72 and the hemostatic closure device 20. The locating device 72 generally includes a proximally positioned and generally cylindrically shaped delivery member 76 having a portion of the locating members 78 slidably retained therein. In this embodiment, the locating device 72 preferably includes at least a pair of semi-circularly shaped guide members 80 which extend distally from the delivery member 76. As shown, the locating members 78 are extendable from the distal end of the guide members 80 and include one or more predetermined bends or curved areas 79 thereon.

Each guide member 80 preferably encloses the distal portion of at least one locating member 78. The locating members 78 of the present embodiment are preferably formed by an elongate wire which extend through common or separate passageways in the guide member 80 to form a loop shaped member 82 at the distal end thereof when the locating members 78 are moved to the extended position. The locating members 78 include an elongate proximal portion 86 which slidably extends through the guide member 80 in the delivery member 76 and an elongate distal portion which slidably extends through the distal end portion of the guide member 80.

Figure 16:
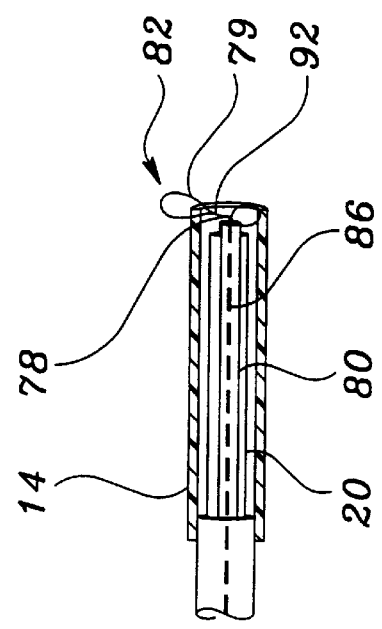
FIG. 16 is a side elevational view, partially in cross section, showing the guideways and locating members with locating members of the alternate form of the locating device of FIG. 14 fully extended from the access sheath.

As shown in FIGS. 15 and 16, the locating members 78 are connected to a proximally positioned knob member 84 which is located along the proximal end of the delivery member 76. The proximal end portion of each locating member 78 is connected to a slidable band or knob member 84 located along the proximal portion of the delivery member 76 such that actuation of the knob member 84 will cause the locating members 78 to form the loop shaped members 82 which extend laterally from the distal end of the guide members 80.

The loop members 82 of the present embodiment preferably consist of a small diameter wire or filament member having a pair of end portions which are fixedly connected to the knob member and extend through guide members 80. When the locating device 50 is initially positioned in the access sheath 14, the guide members 80 of the locating device 72 are positioned adjacent to and along the exterior of the hemostatic closure device 20. In the retracted position, the loop members 82 may be used to assist in the retention of the hemostatic closure device 20 in the desired position in the locating device 72 by causing a small amount of inward deflection of the guide members 80 adjacent to the curved areas 79 of the locating members 78. The slight deflection of the guide members frictionally contacts the side of the distal end portion 22 of the hemostatic closure device 20 in the retracted position of the locating members 78 as shown in FIGS. 14 and 18.

In the preferred form of the present embodiment, when the knob member 84 is rotated, the locating members 78 are moved distally in the guide members 80 and the loop members 82 are formed. The loop members 82 expand and extend laterally from a position beyond the distal end 22 of the hemostatic closure device 20 and access sheath 22. The loop members 82 are also oriented to extend generally perpendicular to the distal end of the access sheath 14. Because the guide members 80 extend lengthwise along the hemostatic closure device 20, the guide members 80 retain the hemostatic closure device 20 in the desired position relative to the locating device 72 as the sealing member 70 is moved to the desired position in the incision.

As shown best in FIGS. 14 and 16, the proximal portion of the delivery member 76 includes the knob member 84 thereon to allow for the extension and retraction of the locating members 78 upon the clockwise or counterclockwise movement of the knob member 84 with respect to the delivery member 76. Although, the movement of the locating members 78 and the formation of the loop members 82 in this embodiment is described as being through the rotational movement of the knob member 84, it is anticipated that this type of movement between extended and retracted positions may also be accomplished by sliding levers or other convenient conventional automatic or manual methods of imparting distal and proximal movement to the locating members 78. In this embodiment, the external surface of the guide members 80 contact only a relatively small amount of the external surface of the hemostatic closure device 20 so that the portion of the hemostatic closure device 20 between the guide members 80 may be allowed to absorb fluids in the incision and expand while the removal of the guide members 80 from the incision does not adversely affect the position of the hemostatic closure device 20 in the incision. Additionally, the external surface of the guide members 80 may include a lubricous coating thereon to assist in the placement and removal of the locating device in the incision.

Once the angiographic or other medical procedure has been performed and the catheter is removed from the patient, the introducer or access sheath 14 is retained in the incision as shown above. The access sheath 14 functions to maintain the incision open while the sealing assembly 70 is inserted therethrough. Once the user confirms that the access sheath 14 is properly positioned in the incision so that the distal end of the access sheath 14 extends a short distance into the artery 10, the user may insert the sealing assembly 70 into the incision and blood vessel by pushing the sealing assembly 70 through an optional hemostasis valve(not shown)in the access sheath 14. The sealing assembly 70 is moved distally with respect to the access sheath 14 until distal end of the guide members 80 and the loop members 82 of the locating device 72 extend slightly beyond the distal end of the access sheath 14.

As with the prior embodiments, the length of the locating device 72 and the access sheath 14 are preferably controlled to allow the user to readily determine when the loop members 82 are properly positioned to extend slightly beyond the distal end of the access sheath 14. For example, the outer surface of the locating device 72 may include markings thereon or other visually, audibly or physically observable indications of when the locating device 72 is properly aligned with the access sheath 14. When the distal end of the guide members 80 and locating members 78 are positioned adjacent to or slightly beyond the distal end of the access sheath 14, the locating device 72 may be rotated with respect to the blood vessel of the patient so that the loop members 82 are oriented to extend upstream and downstream in the blood vessel of the patient when the locating members 78 are extended.

Figure 17:
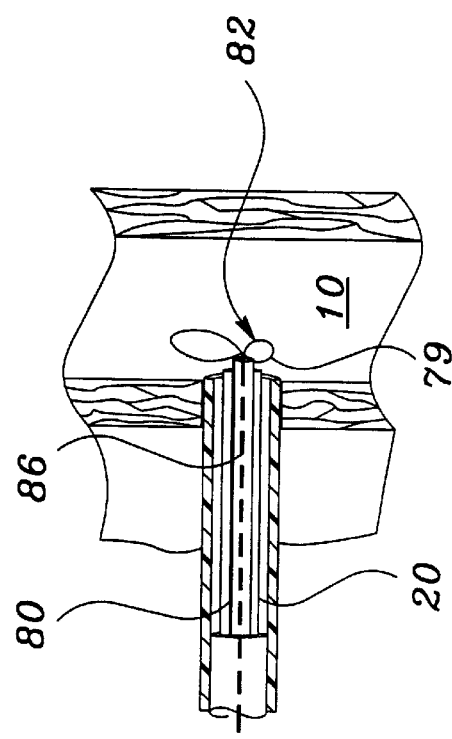
FIG. 17 is a side elevational view, partially in cross section showing the sealing assembly of FIG. 14 with the locating members of the alternate form of the locating device of FIG. 14 fully extended and positioned along the inner wall of the patient's blood vessel.

In the preferred use of the present embodiment, the access sheath 14 is preferably retained in the incision such that the distal end thereof extends slightly into the blood vessel of the patient. The sealing device 70 may then be inserted into the access sheath 14 such that the distal end of the sealing device 70 is aligned with or extends slightly beyond the distal end of the access sheath 14. The knob member 84 of the locating device 72 may then be rotated to move the locating members 78 distally until the loop members 82 are extended. Once the loop members 82 reach the fully extended position, the sealing device 70 and access sheath 14 may be moved proximally in the incision until the loop members 82 contact the wall of the blood vessel as shown in FIG. 17. Thereafter, the access sheath 14 may be removed partially or completely from the incision to expose the hemostatic closure device 20 to the fluids in the incision. After a relatively short period of time, the hemostatic closure device 20 will begin to soften and swell in the incision.

The knob member 84 of the locating device 72 may then be rotated to move the locating members 78 proximally until the loop members 82 are retracted. The locating device 72 and access sheath 14 may then be removed from the incision to leave the hemostatic closure device 20 in the desired position in the incision. The guide members 80 of the locating device 72 are preferably sized to allow the majority of the diameter of the hemostatic closure device 20 to contact the tissue along the incision prior to the removal of the locating device 72 from the incision. This allows the hemostatic closure device 20 to initially receive fluids therein and expand upon itself until the flow of fluid through the incision is prevented. This allows the locating device 72 to be withdrawn from the incision without significantly affecting the position of the hemostatic closure device 20 in the incision.

Additionally, as with the prior embodiments, the distal end portion 22 of the hemostatic closure device 20 is positioned in the incision at or along the outer wall or lumen of the blood vessel or artery 10 so that none of the hemostatic closure device 20 extends into the blood vessel 10 to disrupt the flow of blood therethrough. The porosity of the hemostatic closure device 20 is also preferably chosen so that the hemostatic closure device 20 will expand as it absorbs fluids from the surrounding tissue and so that the hemostatic closure device 20 will degrade in a matter of weeks or months. Because the hemostatic closure device 20 does not extend into the lumen of the blood vessel 10, the hemostatic closure device 20 of the present embodiment may include a clotting agent incorporated therein to promote localized hemostasis in the incision without increasing the likelihood of thrombosis formation in the blood vessel 10.

Another alternate embodiment of the present invention is shown in FIGS. 20–25. In this embodiment, the previously inserted access sheath 14 is retained in the incision after the procedure has been performed. The preloaded sealing assembly 100 is then inserted into the incision through the access sheath 14 in a manner similar to the embodiments described above.

Figure 25:
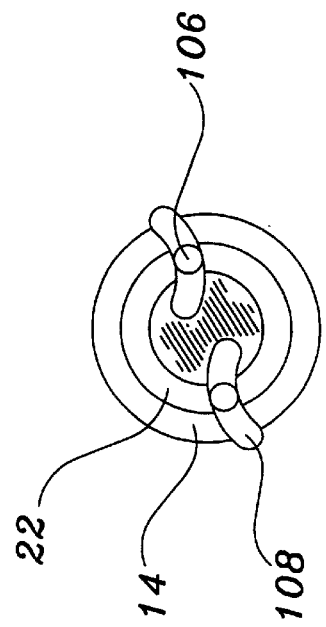
FIG. 25 is a bottom view of the distal end of the sealing assembly of FIG. 20 in the access sheath with the locating members shown in the extended position.
Figure 24:
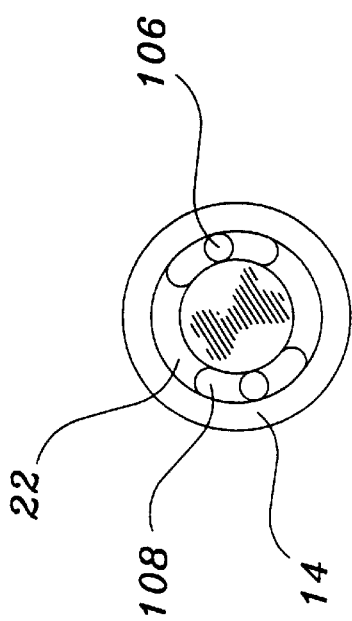
FIG. 24 is a bottom view of the distal end of the sealing assembly of FIG. 20 in the access sheath with the locating members shown in the retracted position.

The sealing assembly 100 of the present embodiment generally consists of the locating device 102 and the hemostatic closure device 20. The locating device 102 generally includes a proximally positioned and generally cylindrically shaped delivery member 104 which, in the present embodiment, includes the proximal ends of the locating members 106 rotatably retained therein. As shown, the locating members 106 extend distally from the delivery member 104 along the sides of the hemostatic closure device 20. The distal end portions 108 of the locating members 106 are preferably curved paddle-shaped members which are preferably oriented generally perpendicular to the longitudinal axis of the locating device 102. In this embodiment, the locating device 102 preferably includes a pair of elongate and relatively small diameter locating members 106 thereon although one or more locating members are believed to be sufficient to perform the locating function as described below. As shown in FIGS. 24 and 25, each of the locating members 106 include an elongate portion which is oriented to extend longitudinally along and through and beyond the passageways 110 formed lengthwise in the delivery member 104 of the locating device 102. The locating members 106 extend distally from the distal end of the delivery member 104 along and adjacent to the outer dimension of the hemostatic closure device 20. The distal end portion 104 of each locating member 106 is generally perpendicular to the lengthwise dimension of the remainder of the locating member 106 and semicircularly shaped from an end view as shown in FIG. 25. The proximal end of the locating members 106 may be formed with knob and spring members 112 thereon which are oriented such that when the distal end portions 108 of the locating device 102 is extended beyond the access sheath 14, the locating members 106 are rotated and the distal end portion 108 of each the locating members 106 is automatically rotated from the retracted position (FIG. 24) to the extended position (FIG. 25). The automatic rotation of the knob members 112, causes the rotation of the locating members 106 in the passageways 110 and along the hemostatic closure device 20 so that the distal end portions 108 of the locating members 106 extend laterally from the distal end of the hemostatic closure device 20 and the access sheath 14.

As shown in FIG. 20, when the locating device 102 is positioned in the access sheath 14, the locating members 106 are positioned adjacent to and along the outer lengthwise dimension of the hemostatic closure device 20 with the distal end portions 108 of the locating members 106 extending slightly beyond the distal end 22 of the hemostatic closure device 20. When the distal end portions 108 of the locating members 106 are rotated to the extended position, the distal end portions 108 of the locating members 106 swing outwardly to extend laterally beyond the outer dimension of the locating device 102 and the access sheath 14. Because the portion of the locating member 106 proximally of the distal end portions 108 does not extend beyond the distal end of the hemostatic closure device 20, the combination of the distal end portions 108 of the locating members 106 and the longitudinal portions of the locating members 106 function to retain the hemostatic closure device 20 in the desired position in the sealing assembly 100 prior final positioning of the hemostatic closure device 20 in the incision. Additionally, as shown in FIG. 25, the distal end portions 108 include a relatively short retaining member which extends inwardly to contact the distal end portion of the hemostatic closure device to ensure that the hemostatic closure device remains in the desired position relative to the distal end portions 108 of the locating device as the locating device 102 is positioned in the incision and blood vessel.

Figure 23B:
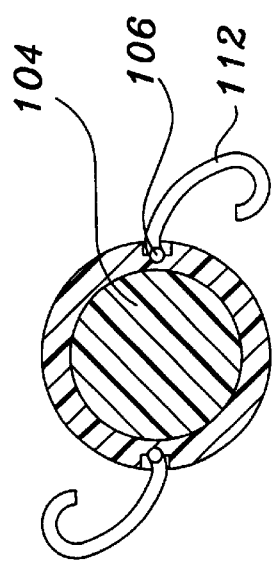
FIGS. 23A and 23B are cross sectional views taken along lines 23—23 of FIG. 20 showing the paddle members of the locating members in the retracted and extended positions, respectively.
Figure 23A:
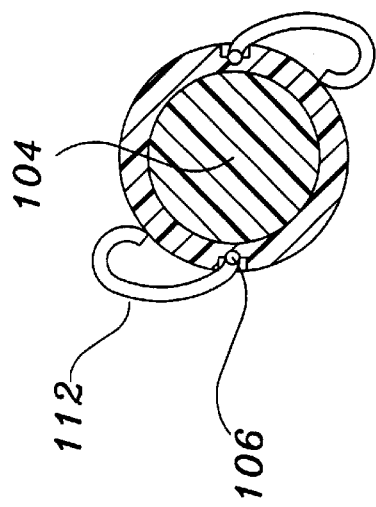

As shown best in FIGS. 23A and 23B, the proximal portion of the delivery member 104 includes the knob and spring members 112. As shown, the knob and spring members 112 consist of an elongate wire member having ends which are bent and under tension to cause the rotation of the distal end portions 108 of the locating device 102 to the laterally extended position. The knob and spring members 112 are connected to the proximal end of the locating members 106 to cause the lateral extension of the distal end portions 108 of the locating members 106. Similarly, the user may grasp and depress the knob members 112 to rotate the locating members 106 and return the distal end portions 108 to a retracted position along the circumference of the delivery member 104. This movement of knob and spring members 112 increases the tension in the knob and spring members 112 and causes the lateral retraction of the distal end portion 108 of the locating members 106. Although the knob members 112 are described as being rotatable, it is anticipated that this type of movement may also be accomplished by sliding levers or other convenient methods of imparting the desired rotational movement to the distal end portions 108 of the locating members 106. Furthermore, although the tension member 112 is shown as a bent wire member which functions similar to a leaf spring, the knob member 112 may be constructed as a conventional coiled or compression spring or other member which biases the knob member 112 to the preferred open position.

Once the angiographic or other medical procedure has been performed and the catheter is removed from the patient, the introducer or access sheath 14 is retained in the incision and blood vessel as shown in FIG. 20. Once the user confirms that the access sheath 14 is properly positioned in the incision with the distal end of the access sheath 14 extending a short distance into the artery 10, the user may insert the sealing assembly 100 into the access sheath 14 and through the incision by pushing the sealing assembly 100 distally while holding the access sheath 14 steady until the distal end portions 108 of the locating members 106 extend adjacent to or slightly beyond the distal end of the access sheath 14. The length of the locating device 102 and the access sheath 14 are tightly controlled to allow the user to readily determine when the locating members 106 are properly positioned with respect to the distal end of the access sheath 14 as shown in FIG. 21. With the present embodiment, when the distal end portions 108 of the locating members 106 pass beyond the distal end of the access sheath 14, the knob member 112 will provide the user with a clear visual indication that the distal end portions 108 are no longer constrained by the access sheath 14. For example, the outer surface of the locating device 102 may include markings thereon (not shown) or other visually, audible or physically observable indications of when the locating device 102 is properly aligned with respect to the access sheath 14. When the locating members 106 are positioned slightly beyond the distal end of the access sheath 14, the knob members 112 of the present embodiment will automatically spring outwardly to signal to the user that the distal end portions 108 of the locating members 106 are located beyond the distal end of the access sheath 14 and are fully extended to a position which is generally perpendicular to the outer dimension of the access sheath 14 into the blood vessel of the patient.

Once the locating members 106 are rotated to the extended position, the locating device 102 and access sheath 14 may be moved proximally in the incision until the extended distal end portions 108 of the locating members 106 contact the wall of the blood vessel as shown in FIG. 22. As with the prior embodiments, the distal end portions 108 of the locating members 106 are designed to provide the user with a sufficient indication of the contact between the distal end portions 108 of the locating members 106 and the wall of the blood vessel to confirm the proper positioning of the locating device 102 in the incision and blood vessel. Once the distal end portions 108 of the locating members 106 are positioned along the wall of the blood vessel, the access sheath 14 may be removed partially or fully from the incision. The knob members 112 on the locating device 102 may then be grasped to rotate the distal end portions 108 to a position which is in line with the periphery of the locating device 102. This movement of the knob members 112 causes the distal end portions 108 of the locating members 106 to rotate to the retracted position. Thereafter, the locating device 102 may be removed from the incision while the hemostatic closure device 20 remains in the incision to obstruct the flow of fluids therethrough.

As with the prior embodiments, the length of the distal end portions 108 and the thickness of the locating members 106 are chosen so that the majority the hemostatic closure device 20 is allowed to absorb fluids in the incision while the hemostatic closure device 20 remains in the locating device 102. The absorption of fluids by the hemostatic closure device 20 causes the hemostatic closure device 20 to resist movement in the incision as the locating device 102 is removed from the incision. Additionally, the external surface of the distal end portions 108 of the locating members 106 may be coated with lubricous coatings, such as various commercially available hydrophilic and/or water activated coatings, to increase to lubricity of the external surface of the locating members 106 to ease the removal of the locating device 102 from the incision.

The distal end 22 of the hemostatic closure device 20 of this embodiment is preferably positioned in the incision at or along the outer wall or lumen of the blood vessel or artery 10 so that none of the hemostatic closure device 20 extends into the blood vessel 10 to disrupt the flow of blood therethrough. The porosity of the hemostatic closure device 20 is preferably chosen so that the hemostatic closure device 20 will expand as it absorbs fluids from the surrounding tissue and so that the hemostatic closure device 20 will degrade in a matter of weeks or months. Because the hemostatic closure device 20 does not extend into the lumen of the blood vessel 10, the hemostatic closure device 20 of the present embodiment may include a clotting agent incorporated therein to promote localized hemostasis in the incision without increasing the likelihood of thrombosis formation in the blood vessel 10.

While the preferred forms of the present invention are described and illustrated herein, it will be obvious to those skilled in the art that various changes and modifications may be made thereto without departing from the scope of the present invention as defined by the following claims. For example, it is anticipated that the proximal end portion of the locating device may include a stabilizing rod extending therethrough to retain the hemostatic closure device in the desired position in the incision as the locating device is removed from the incision.

What is claimed is:

1. A sealing assembly for sealing an incision formed in a patient's body wherein the incision extends from the skin of a patient into a target organ or blood vessel of a patient, said sealing assembly comprising:

an elongate hemostatic closure device having a longitudinal axis, distal and proximal ends and an outer surface, said hemostatic closure device adapted to be received in the incision such that said distal end is located at a first predetermined position in the incision along the outer surface of a target organ or blood vessel of a patient and said proximal end is located at a second predetermined position along the outer surface of the incision adjacent to the skin of a patient; and an elongate locating device having a proximal end portion positioned generally adjacent to said proximal end portion of said hemostatic closure device and at least one locating member having a longitudinal axis thereon, said at least one locating member being non-coaxial with said elongate hemostatic closure device; wherein in use, said at least one locating member being dimensioned so as to extend along a portion of said outer surface of said hemostatic closure device while the remainder of said outer surface of said hemostatic closure device is in contact with tissue surrounding the incision.

2. The sealing assembly of claim 1 wherein said at least one locating member extends along less than one half of said outer dimension of said hemostatic closure device.

3. The sealing assembly of claim 1 wherein said at least one locating member includes at least a portion thereof which is movable between first and second positions to assist in the positioning of said hemostatic closure device in the predetermined position in the incision.

4. The sealing assembly of claim 1 wherein said at a portion of said at least one locating member is movable between said first position wherein said locating member is generally aligned with the lengthwise dimension of said locating device and a second position wherein at least a portion of said locating member extends laterally therefrom.

5. The sealing assembly of claim 1 wherein said proximal end of said locating device includes a tubular body portion and said at least one locating member extends distally thereof to allow for the removal of said locating device from the incision or puncture without dislocation of said hemostatic closure device from a predetermined positioned in the incision.

6. The sealing assembly of claim 5 wherein said hemostatic closure device is preloaded in said locating device and said tubular body portion includes a stabilizing member associated therewith.

7. The sealing assembly of claim 1 wherein said at least one locating member is movable along said outer surface of said hemostatic closure device between first and second positions without moving the hemostatic closure device relative to the remainder of said locating device.

8. The sealing assembly of claim 1 wherein said at least one locating member is movable between a first position and a second position wherein said at least one locating member is oriented to extend generally along a lengthwise dimension of said hemostatic closure device in said first position and at least a portion of said at least one locating member extends generally laterally from the longitudinal dimension of said locating device in said second position.

9. The sealing assembly of claim 8 wherein said at least one locating member is extendable from said first position to said second position and retractable from said second position to said first position.

10. The sealing assembly of claim 1 wherein said at least one locating member includes a distal end portion having a loop shaped member thereon.

11. The sealing assembly of claim 1 wherein said at least one locating member includes a distal end portion having a paddle member thereon.

12. The sealing assembly of claim 1 wherein said at least one locating member includes an elongate proximal portion and a distal end portion wherein said distal end portion is oriented generally perpendicular to the lengthwise dimension of said proximal portion.

13. A sealing assembly for sealing an incision formed a patient's body wherein the incision extends generally from the skin of a patient into a target organ of blood vessel of a patient, said sealing assembly comprising in combination:

an elongate locating device having distal and proximal ends and at least one locating member forming part of said distal end and an actuation member associated therewith wherein actuation of said actuation member moves said locating member from a first position wherein said at least one locating member having a longitudinal axis is generally longitudinally aligned with the longitudinal dimension of said locating device to a second position wherein at least a portion of said at least one locating member extends laterally from the longitudinal dimension of said locating device; and a biodegradable and generally elongate hemostatic closure device having a longitudinal axis and adapted to be positioned in a first predetermined position in said locating device with said at least one locating member generally aligned non-coaxially along said longitudinal axis of said hemostatic closure device, wherein said hemostatic closure device is further adapted to be retained in a second predetermined position in the incision in the patient after said locating device is removed from the incision.

14. The sealing assembly of claim 13 wherein said locating device includes a proximal member positioned proximally of said hemostatic closure device and said at least one locating member includes a portion thereof which extends along and distally beyond said proximal member and said hemostatic closure device.

15. The sealing assembly of claim 13 wherein said hemostatic closure device is an elongate and generally rod-shaped member having an outer surface and said locating member of said locating device contacts a portion of said outer surface prior to the insertion of said hemostatic closure device in said second predetermined position.

16. The sealing assembly of claim 15 wherein said portion of said outer surface of said hemostatic closure device contacted by said locating member is in contact with less than the entire outer surface of said hemostatic closure device prior to the insertion of said hemostatic closure device in said second predetermined position.

17. The sealing assembly of claim 13 wherein said locating member is movably received in a guide member which is positioned along generally along said lengthwise dimension of said hemostatic closure device.

18. The sealing assembly of claim 17 wherein said guide member is a generally cylindrically shaped member.

19. The sealing assembly of claim 17 wherein said guide member has a generally semicircular cross sectional shape.

20. The sealing assembly of claim 17 wherein said at least one locating member is movable between retracted and extended positions and a distal portion of said locating member is a loop shaped member in said extended position of said locating member.

21. A sealing assembly for sealing an incision formed in the body of a patient wherein the incision extends generally from the skin of the patient into a target organ or blood vessel of the patient, said sealing assembly comprising in combination:

a generally elongate hemostatic closure device having an outer surface and distal and proximal ends adapted to be inserted into the incision of the patient such that said distal end of said hemostatic closure device generally conforms to the outer surface of the target organ or blood vessel of the patient and said proximal end is adapted to be received in the incision proximally thereof; and a locating device having proximal and distal end portions and said proximal end portion is in contact with said proximal end portion of said hemostatic closure device and includes an actuation member associated therewith and said distal end portion includes a locating member generally aligned along and in contact with less than the entire outer surface of said hemostatic closure device wherein actuation of said actuation member increases the radial circumference of said distal end portion to facilitate the placement of said distal end of said hemostatic closure device in a desired position in the incision.

22. The sealing assembly of claim 21 wherein said hemostatic closure device includes an elongate outer surface and said locating member contacts less than one half of said outer surface of said hemostatic closure device.

23. The sealing assembly of claim 21 wherein said locating member extends beyond said distal end of said hemostatic closure device such that said distal end of said locating member is opeoratively positionable into contact with a portion of the target organ or blood vessel of the patient.

24. A method of sealing an incision formed in a patient's body wherein the incision extends generally from the skin of the patient into a blood vessel of the patient, the method comprising:

inserting a sealing assembly having a locating device with a proximal end member and at least one locating member through the previously formed incision and into the blood vessel of the patient, wherein the locating member has a relatively small diameter with respect to the locating device;

pushing the sealing assembly into the incision such that the proximal end portion of the locating device is in contact with the hemostatic closure device during insertion;

causing the lateral extension of the locating member;

withdrawing the laterally extended locating member from the incision and blood vessel until the locating member contacts a predetermined portion of the inner wall of the blood vessel;

retracting the laterally extended locating member and leaving a hemostatic closure device in a desired position in the incision;

withdrawing the locating device from the incision while the hemostatic closure device is retained in the incision.

25. A sealing assembly for sealing an incision formed in a patient's body wherein the incision extends generally from the skin of a patient into a target organ or blood vessel of a patient, said sealing assembly comprising in combination:

an elongate locating device having a longitudinal axis, distal and proximal ends and at least one locating member forming part of said distal end and an automatic actuation member associated therewith wherein actuation of said actuation member moves said locating member from a first position wherein said at least one locating member is generally longitudinally aligned with the longitudinal dimension of said locating device to a second position wherein at least a portion of said at least one locating member extends laterally from the longitudinal dimension of said locating device and wherein said locating device is manually movable from said second position to said first position; and a biodegradable and generally elongate hemostatic closure device having a longitudinal axis, adapted to be positioned in a first predetermined position in said locating device with said at least one locating member generally non-coaxially aligned along said longitudinal axis of said hemostatic closure device and at least a portion of said locating device is positioned proximally of said hemostatic closure device in use and wherein said hemostatic closure device is further adapted to be retained in a second predetermined position in the incision in the patient after said locating device is removed from the incision.

\* \* \* \* \*